United States Patent
Takahashi

(10) Patent No.: US 9,974,981 B2
(45) Date of Patent: May 22, 2018

(54) DEVICE FOR CONTROLLING RADIATION THERAPY DEVICE, RADIATION THERAPY SYSTEM, METHOD FOR CONTROLLING RADIATION THERAPY DEVICE, AND PROGRAM

(71) Applicant: HITACHI, LTD., Tokyo (JP)

(72) Inventor: Kunio Takahashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 211 days.

(21) Appl. No.: 14/906,794

(22) PCT Filed: Oct. 8, 2013

(86) PCT No.: PCT/JP2013/077311
§ 371 (c)(1),
(2) Date: Jan. 21, 2016

(87) PCT Pub. No.: WO2015/052766
PCT Pub. Date: Apr. 16, 2015

(65) Prior Publication Data
US 2016/0166858 A1    Jun. 16, 2016

(51) Int. Cl.
*A61N 5/10* (2006.01)

(52) U.S. Cl.
CPC ......... *A61N 5/1082* (2013.01); *A61N 5/1048* (2013.01); *A61N 5/1081* (2013.01)

(58) Field of Classification Search
CPC ... A61N 5/1081; A61N 5/1048; A61N 5/1082
See application file for complete search history.

(56) References Cited

U.S. PATENT DOCUMENTS

| 2004/0005027 | A1* | 1/2004 | Nafstadius | A61N 5/1049 378/65 |
| 2011/0129060 | A1 | 6/2011 | Handa et al. | |
| 2012/0134470 | A1* | 5/2012 | Shibuya | A61N 5/1065 378/65 |

FOREIGN PATENT DOCUMENTS

| GB | 2471749 A | 1/2011 |
| JP | 2006-174885 A | 7/2006 |
| JP | 2009-297324 A | 12/2009 |

(Continued)

OTHER PUBLICATIONS

Europe Patent Office, "Search Report for European Patent Application No. 13895243.7," dated Jul. 18, 2016.

(Continued)

*Primary Examiner* — Christine H Matthews
*Assistant Examiner* — Joshua D Lannu

(57) ABSTRACT

This device for controlling a radiation treatment device is provided with a gantry for supporting a radiation emitting device so as to enable rotation thereof about a first axis, and a ring for supporting the gantry so as to enable rotation thereof about a second axis intersecting with the first axis, the device for controlling a radiation treatment device being provided with a movement path information storage unit for storing movement path information set in the radiation emitting device, and a control unit for providing a limit to the rotation speed of the gantry and the rotation speed of the ring while maintaining the ratio of the rotation speed of the gantry and the rotation speed of the ring indicated by the movement path information, on the basis of the rotation angle of the gantry and the rotation angle of the ring.

6 Claims, 4 Drawing Sheets

(56) References Cited

FOREIGN PATENT DOCUMENTS

| JP | 2014-113242 A | 6/2014 |
|---|---|---|
| WO | 2007/124760 A1 | 11/2007 |
| WO | 2010/073308 A1 | 7/2010 |

OTHER PUBLICATIONS

PCT/ISA/210, "International Search Report for International Application No. PCT/JP2013/077311," dated Jan. 14, 2014.
PCT/ISA/237, "Written Opinion of the International Searching Authority for International Application No. PCT/JP2013/077311," dated Jan. 14, 2014.

* cited by examiner

DEVICE FOR CONTROLLING RADIATION
THERAPY DEVICE, RADIATION THERAPY
SYSTEM, METHOD FOR CONTROLLING
RADIATION THERAPY DEVICE, AND
PROGRAM

RELATED APPLICATIONS

The present application is National Phase of International Application No. PCT/JP2013/077311 filed Oct. 8, 2013 the disclosure of which is hereby incorporated by reference herein in its entirety.

TECHNICAL FIELD

The present invention relates to a device for controlling a radiation therapy device, a radiation therapy system, a method for controlling a radiation therapy device, and program.

BACKGROUND ART

A radiation therapy device, in which an irradiation device (radiation source) is supported in such a way as to be able to rotate around a diseased site, is known. The rotation of the irradiation device allows the irradiation device to irradiate the diseased site with radiation beams from various directions. Accordingly, it is possible to reduce an irradiation dose to each of the surrounding normal tissues while securing an irradiation dose required to treat the diseased site.

A radiation therapy device, in which the rotation axis of an irradiation device can be rotated, is known. For example, in a radiation therapy device disclosed in PTL 1, an O-shaped ring supports a traveling gantry, and the traveling gantry supports a therapeutic irradiation device via a swing mechanism. The rotation of the O-shaped ring and the traveling gantry allows the therapeutic irradiation device to move in three dimensions. Accordingly, the therapeutic irradiation device is capable of irradiating a diseased site with radiation beams from various directions, and more reliably reducing an irradiation dose to a vulnerable site.

CITATION LIST

Patent Literature

[PTL 1] Pamphlet of International Publication No. WO 2010/073308

SUMMARY OF INVENTION

Technical Problem

The consideration of the path of the irradiation device may be required to be taken into account in designing a radiation therapy device in which the rotation axis of the irradiation device is capable of being rotated. For example, in the radiation therapy device in which the irradiation device rotates around a couch on which a patient lies, when the angle of the rotation axis of the irradiation device with respect to a longitudinal direction of the couch is changed, the distance between the irradiation device and the couch may be changed. The angle of the rotation axis of the irradiation device with respect to the longitudinal direction of the couch may cause the couch to block the path of the irradiation device such that a therapy plan cannot be executed.

The present invention provides a device for controlling a radiation therapy device, a radiation therapy system, a method for controlling a radiation therapy device, and a program by which it is possible to more easily secure a path on which a radiation therapy device is capable of actually moving.

Solution to Problem

According to a first aspect of the present invention, there is provided a device for controlling a radiation therapy device which includes a gantry by which an irradiation device is supported in such a way as to be able to rotate around a first axial line, and a ring by which the gantry is supported in such a way as to be able to rotate around a second axial line intersecting with the first axial line, the device including: a movement path information storage unit configured to store information regarding a movement path set for the irradiation device; and a control unit configured to set a limitation to the rotational speeds of the gantry and the ring while maintaining the ratio between the rotational speed of the gantry and the ring, which is indicated by the information regarding the movement path, based on the rotational angles of the gantry and the ring.

The device for controlling a radiation therapy device may further include a speed limitation map storage unit configured to store a speed limitation map illustrating a relationship between the rotational angles of the gantry and the ring and a limitation to the rotational speeds of the gantry and the ring. The control unit may set a limitation to the rotational speeds of the gantry and the ring based on the speed limitation map.

The device for controlling a radiation therapy device may further include an operation input unit configured to receive an operation input giving an instruction for the movement speed of the irradiation device. The control unit may set a limitation to the rotational speeds of the gantry and the ring while maintaining the ratio between the rotational speeds of the gantry and the ring, which is indicated by the information regarding the movement path, based on the operation input and the rotational angles of the gantry and the ring.

According to a second aspect of the present invention, there is provided a radiation therapy system including a gantry by which an irradiation device is supported in such a way as to be able to rotate around a first axial line; a ring by which the gantry is supported in such a way as to be able to rotate around a second axial line intersecting with the first axial line; a movement path information storage unit configured to store information regarding a movement path set for the irradiation device; and a control unit configured to set a limitation to the rotational speeds of the gantry and the ring while maintaining the ratio between the rotational speed of the gantry and the ring, which is indicated by the information regarding the movement path, based on the rotational angles of the gantry and the ring.

According to a third aspect of the present invention, there is provided a method for controlling a radiation therapy device by which a device for controlling a radiation therapy device, which includes a movement path information storage unit storing information regarding a movement path set for an irradiation device, controls a radiation therapy device including a gantry by which the irradiation device is supported in such a way as to be able to rotate around a first axial line, and a ring by which the gantry is supported in such a way as to be able to rotate around a second axial line intersecting with the first axial line, the method including: a control step of setting a limitation to the rotational speeds of the gantry and the ring while maintaining the ratio between the rotational speeds of the gantry and the ring, which is indicated by the information regarding the movement path, based on the rotational speeds of the gantry and the ring.

According to a fourth aspect of the present invention, there is provided a program in a computer of a device for controlling a radiation therapy device including a gantry by which an irradiation device is supported in such a way as to be able to rotate around a first axial line, and a ring by which the gantry is supported in such a way as to be able to rotate around a second axial line intersecting with the first axial line, with the device for controlling a radiation therapy device including a movement path information storage unit configured to store information regarding a movement path set for the irradiation device, the program causing the computer to execute a control step of setting a limitation to the rotational speeds of the gantry and the ring while maintaining the ratio between the rotational speeds of the gantry and the ring, which is indicated by the information regarding the movement path, based on the rotational angles of the gantry and the ring.

Advantageous Effects of Invention

According to a device for controlling a radiation therapy device, a radiation therapy system, a method for controlling a radiation therapy device, and a program, it is possible to more easily secure a path on which a radiation therapy device is capable of actually moving.

DESCRIPTION OF EMBODIMENTS

Hereinafter, an embodiment of the present invention will be described; however, the claims of the invention are not limited to the embodiment. All combinations of characteristics described in the embodiment are not necessarily essential for the invention to solve problems.

Figure 1:
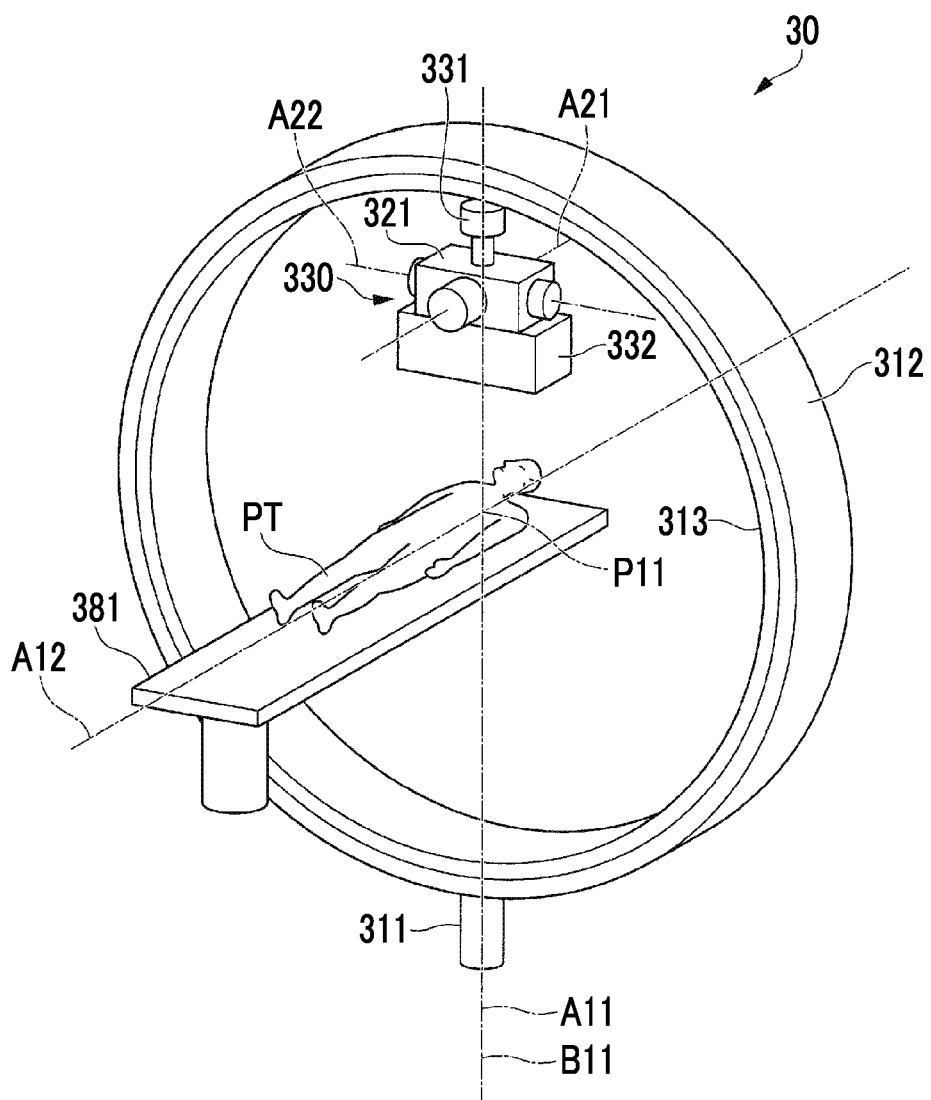
FIG. 1 is a schematic view illustrating the configuration of a radiation therapy device in an embodiment of the present invention.

FIG. 1 is a schematic view illustrating the configuration of a radiation therapy device in an embodiment of the present invention. In FIG. 1, a radiation therapy device 30 includes a turning drive device 311; a ring 312; a gantry 313; a swing mechanism 321; an irradiation unit 330; and a couch 381. The irradiation unit 330 includes an irradiation device 331 and a multileaf collimator (MLC) 332.

The turning drive device 311 rotatably supports the ring 312 above the ground, and rotates the ring 312 around the rotation axis A11. The rotation axis A11 is a vertical axis.

The ring 312 is formed in the shape of a ring centered around a rotation axis A12. The gantry 313 is supported by the ring 312 in such a way as to be able to rotate around the rotation axis A12. The rotation axis A12 is a horizontal axis (that is, an axis perpendicular to the vertical direction), and is orthogonal to the rotation axis A11 at an isocenter P11. The rotation axis A12 is fixed with respect to the ring 312. That is, the rotation axis A12 rotates around the rotation axis A11 upon the rotation of the ring 312.

The gantry 313 and each component installed on the gantry 313 integrally rotate around the rotation axis A11 upon the rotation of the ring 312. Particularly, the irradiation device 331 rotates around the rotation axis A11 upon the rotation of the ring 312.

The gantry 313 is formed in the shape of a ring centered around the rotation axis A12, and is disposed on the inside of the ring 312 to be concentric with the ring 312. The radiation therapy device body 30 further includes a traveling drive device (not illustrated). The gantry 313 is rotated around the rotation axis A12 using driving power from the traveling drive device.

Each component installed on the gantry 313 integrally rotates around the rotation axis A12 upon the rotation of the gantry 313. Particularly, the irradiation device 331 rotates around the rotation axis A12 upon the rotation of the gantry 313.

The rotation axis A12 is an example of a first axial line. The rotation axis A11 is an example of a second axial line. As described above, the irradiation device 331 is supported by the gantry 313 in such a way as to be able to rotate around the first axial line extending in a horizontal direction. The gantry 313 is supported by the ring 312 in such a way as to be able to rotate around the second axial line extending in the vertical direction orthogonal to the first axial line.

The swing mechanism 321 is fixed to the gantry 313 on the inside of the ring, and the irradiation unit 330 is supported by the gantry 313 via the swing mechanism 321. The swing mechanism 321 rotates the irradiation unit 330 around a pan axis A21, and rotates the irradiation unit 330 around a tilt axis A22.

The pan axis A21 is an axis parallel with the rotation axis A12, and is fixed with respect to the gantry 313. The swing mechanism 321 swings the irradiation unit 330 rightward and leftward (that is, rightward and leftward with respect to a patient PT) around the rotation axis A12 by rotating the irradiation unit 330 around the pan axis A21.

The tilt axis A22 is an axis orthogonal to the pan axis A21, and is fixed with respect to the gantry 313. The swing mechanism 321 swings the irradiation unit 330 toward the rotation axis A12 (that is, upward and downward with respect to the patient PT) by rotating the irradiation unit 330 around the tilt axis A22.

The irradiation unit 330 irradiates a diseased site with a therapeutic radiation beam B11 having an irradiation field corresponding to the shape of the diseased site.

Since the irradiation device 331 is supported by the gantry 313 via the swing mechanism 321, once the irradiation device 331 is aimed at the isocenter P11 by the adjustment of the swing mechanism 321, even if the ring 312 is rotated by the turning drive device 311, and the gantry 313 is rotated by the traveling drive device, the therapeutic radiation beam B11 always passes through substantially the isocenter P11. Accordingly, the irradiation device 331 rotates around the rotation axis A11 or A12 such that the irradiation device 331 is capable of irradiating the isocenter P11 with the therapeutic radiation beam B11 from various directions.

The multileaf collimator 332 blocks a portion of the therapeutic radiation beam B11 such that the shape of the irradiation field when the patient is irradiated with the therapeutic radiation beam B11 conforms to the shape of a diseased site.

The couch 381 is a configuration element on which the patient PT lies.

Figure 2:
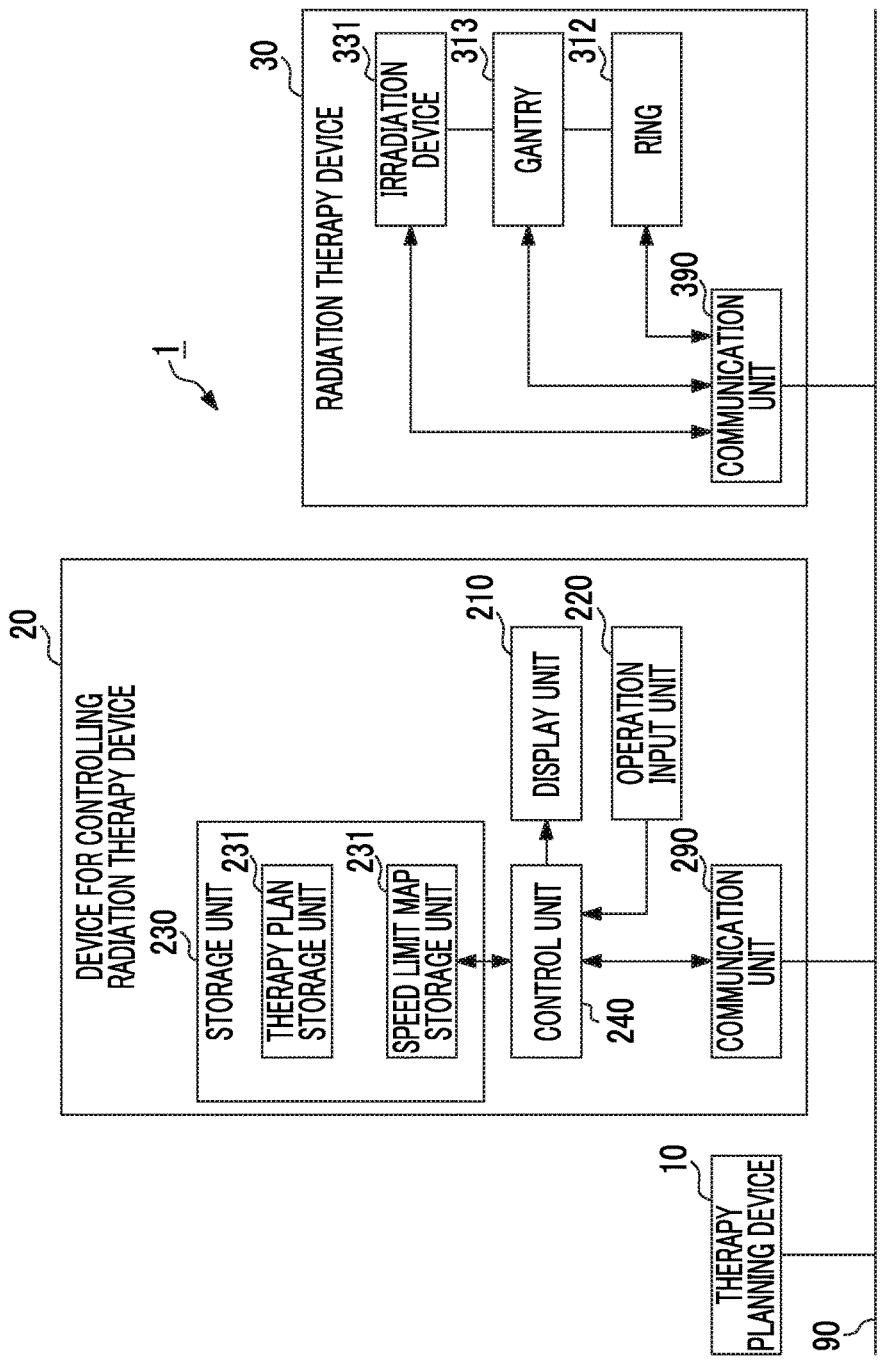
FIG. 2 is a schematic block diagram illustrating the functional configuration of a radiation therapy system in the embodiment.

FIG. 2 is a schematic block diagram illustrating the functional configuration of a radiation therapy system in the embodiment. In FIG. 2, a radiation therapy system 1 includes a therapy planning device 10; a device 20 for controlling a radiation therapy device; the radiation therapy device 30; and a communication channel 90. The device 20 for controlling a radiation therapy device includes a display unit 210; an operation input unit 220; a storage unit 230; a control unit 240; and a communication unit 290. The storage unit 230 includes a therapy plan storage unit 231 and a speed limitation map storage unit 232. FIG. 2 illustrates the ring 312, the gantry 313, and the irradiation device 331 among the components of the radiation therapy device 30 illustrated in FIG. 1. The radiation therapy device 30 further includes a communication unit 390.

The therapy planning device 10, the communication unit 290 of the device 20 for controlling a radiation therapy device, and the communication unit 390 of the radiation therapy device 30 are connected to each other via the communication channel 90. Communication between the devices is performed via the communication channel 90.

The therapy planning device 10 generates a therapy plan for radiation therapy. The therapy plan generated by the therapy planning device 10 contains an instruction regarding a rotational speed set for the radiation therapy device 30. The movement path of the irradiation device 331 is indicated by an instruction regarding the rotational speeds of the gantry 313 and the ring 312 contained in the therapy plan generated by the therapy planning device 10.

Particularly, the therapy planning device 10 generates a therapy plan by which irradiation is performed using dynamic wave arc. The dynamic wave arc is an irradiation method by which the irradiation device 331 continuously irradiates a diseased site with radiation beams with the gantry 313 being continuously rotated, and the ring 312 is rotated simultaneously. It is possible to continuously irradiate a specific site, for example, a diseased site with radiation beams from various directions using the dynamic wave arc. According to the dynamic wave arc, it is possible to more reliably reduce an irradiation dose to a vulnerable site while more efficiently performing radiation therapy with continuous irradiation.

The therapy planning device 10 is configured to include a computer such as a personal computer (PC).

The device 20 for controlling a radiation therapy device controls the radiation therapy device 30 based on the therapy plan transmitted from the therapy planning device 10. Specifically, the device 20 for controlling a radiation therapy device generates control signals to control the radiation therapy device 30 based on the therapy plan, and transmits the control signals to the radiation therapy device 30.

The device 20 for controlling a radiation therapy device is configured to include a computer such as a personal computer.

The display unit 210 is configured to include a display screen such as a liquid crystal panel, and displays various pieces of information. For example, the display unit 210 displays error information when an error occurs in the radiation therapy device 30.

The operation input unit 220 is configured to include an input device such as a keyboard and a mouse, and receives an operation input from an operator (for example, a radiation therapy technician) of the radiation therapy system 1. For example, the operation input unit 220 receives an operator's operation giving an instruction for the start of irradiation.

The operation input unit 220 receives an operator's operation giving an instruction for the start of operation of the radiation therapy device 30 prior to the start of irradiation so as to confirm the path of the irradiation device 331. Hereinafter, the operator of the radiation therapy system 1 is simply referred to as an "operator".

The storage unit 230 is configured to include a storage device of the device 20 for controlling a radiation therapy device, and stores various pieces of information.

The therapy plan storage unit 231 stores information regarding a movement path set for the irradiation device 331. Specifically, the therapy plan generated by the therapy planning device 10 contains the movement path of the irradiation device 331. The therapy plan storage unit 231 stores the therapy plan received by the communication unit 290 from the therapy planning device 10.

The speed limitation map storage unit 232 stores a speed limitation map in advance. The speed limitation map stored in the speed limitation map storage unit 232 illustrates a relationship between the rotational angles of the gantry 313 and the ring 312 and a limitation to the rotational speeds of the gantry 313 and the ring 312.

The control unit 240 executes various functions by controlling each unit of the device 20 for controlling a radiation therapy device. A central processing unit (CPU) of the device 20 for controlling a radiation therapy device reads a program from the storage device of the device 20 for controlling a radiation therapy device such that the control unit 240 is realized.

Particularly, the control unit 240 generates control signals to control the radiation therapy device 30 according to the therapy plan from the therapy planning device 10. The control signals generated by the control unit 240 contain information regarding control of the rotational speed of the gantry 313, and information regarding control of the rotational speed of the ring 312.

The control unit 240 sets a limitation to the rotational speeds of the gantry 313 and the ring 312 based on the rotational angles of the gantry 313 and the ring 312. Specifically, the control unit 240 sets a limitation to the rotational speeds of the gantry 313 and the ring 312 in a region of the speed limitation map in which the rotational speed of the gantry 313 or the ring 312 is limited, based on the speed limitation map stored in the speed limitation map storage unit 232.

More specifically, when at least one of the rotational speeds of the gantry 313 and the ring 312 contained in the therapy plan exceeds a limit value illustrated in the speed limitation map, the control unit 240 reduces the rotational speeds of the gantry 313 and the ring 312 to values less than the rotational speeds indicated in the therapy plan.

At this time, the control unit 240 reduces the rotational speeds of the gantry 313 and the ring 312 while maintaining the ratio between the rotational speed of the gantry 313 and the rotational speed of the ring 312 which are indicated in the therapy plan. Accordingly, the control unit 240 is capable of reducing the rotational speeds of the gantry 313 and the ring 312 without causing the deviation of the movement path of the irradiation device 331 from the path in the therapy plan.

The communication unit 290 communicates with the therapy planning device 10 and the radiation therapy device 30 via the communication channel 90. Particularly, the communication unit 290 receives the therapy plan from the therapy planning device 10. The communication unit 290 transmits control signals to the radiation therapy device 30 so as to operate the gantry 313, the ring 312, or the like. The communication unit 290 receives information regarding the state of the radiation therapy device 30, for example, information regarding the rotational angle of the gantry 313 and information regarding the rotational angle of the ring 312, from the radiation therapy device 30.

The communication unit 390 of the radiation therapy device 30 communicates with the communication unit 290 of the device 20 for controlling a radiation therapy device. Particularly, the communication unit 390 receives control signals from the communication unit 290. The communication unit 390 transmits information regarding the state of the radiation therapy device 30 to the communication unit 290.

Hereinafter, a limitation to the rotational speed of the gantry 313 or the ring 312 will be described with reference to FIG. 3.

Figure 3:
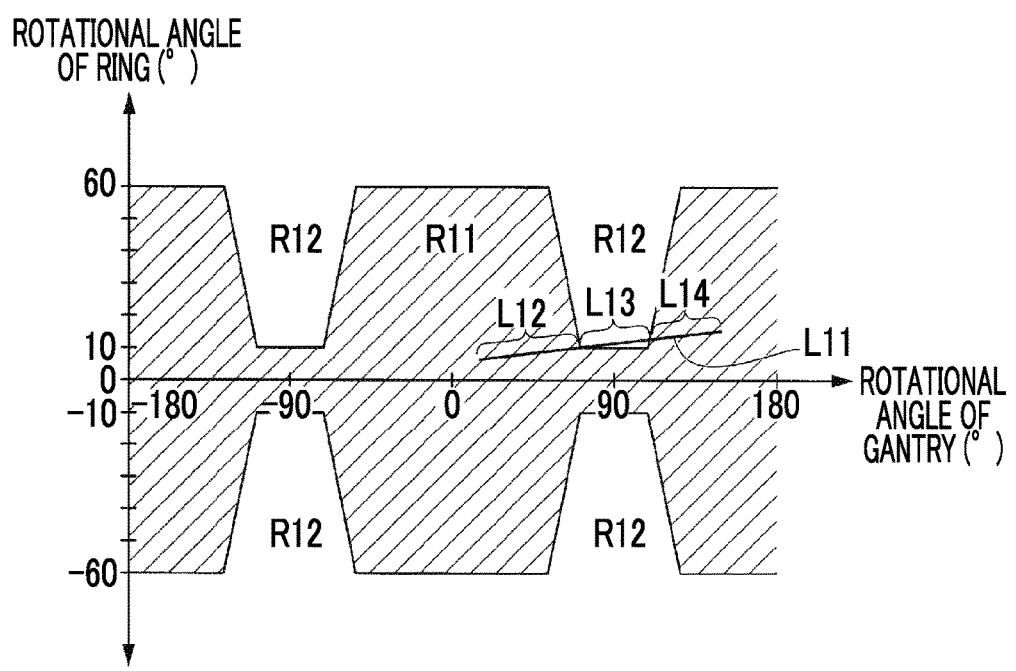
FIG. 3 is a view illustrating an example of a speed limitation map stored in a speed limitation map storage unit 232 in the embodiment.

FIG. 3 is a view illustrating an example of a speed limitation map stored in the speed limitation map storage unit 232. In FIG. 3, the speed limitation map is illustrated in a graphic form.

The horizontal axis of the graph in FIG. 3 represents the rotational angle of the gantry 313. The rotational angle of the gantry 313 when the irradiation device 331 is present at the highest position as illustrated in FIG. 1 is deemed to be 0 degrees (0°), the rightward rotation when the radiation therapy device 30 is seen from the feet side of the patient PT is deemed to be positive, and the range of one rotation from −180 degrees to 180 degrees is illustrated along the horizontal axis.

The vertical axis of the graph in FIG. 3 represents the rotational angle of the ring 312. The rotational angle of the ring 312 when the rotation axis A12 is aligned with a longitudinal direction of the couch 381 as illustrated in FIG. 1 is deemed to be 0 degrees, the rightward rotation when the ring 312 is seen from the upper side is deemed to be positive, and a range from −60 degrees to 60 degrees is illustrated along the vertical axis.

In FIG. 3, a cross-hatched region R11 is a region in which the rotational speeds of the gantry 313 and the ring 312 are not limited. In contrast, a region R12 is a region in which the rotational speeds of the gantry 313 and the ring 312 are limited. The region R12 is a region other than the region R11.

In the speed limitation map illustrated in FIG. 3, a region in which caution is required to prevent contact between the irradiation device 331 and the couch 381 is the region in which the rotational speeds of the gantry 313 and the ring 312 are limited. When the rotation axis A12 of the gantry 313 is offset from the longitudinal direction of the couch 381 due to the rotation of the ring 312, and the irradiation device 331 is proximate to the couch 381 due to the rotation of the gantry 313, the irradiation device 331 may come into contact with the couch 381 due to the rotational angle of the ring 312 or the gantry 313.

The control unit 240 controls the radiation therapy device 30 according to the speed limitation map. For example, when the path of rotation of the gantry 313 and the ring 312 is a line L11, the control unit 240 does not limit the rotational speed of the gantry 313 or the ring 312 in a line segment L12 and a line segment L14. At this time, the control unit 240 generates control signals to control the gantry 313 or the ring 312 according to the rotational speed of the gantry 313 or the ring 312 contained in the therapy plan.

In contrast, the device 20 for controlling a radiation therapy device limits the rotational speed of the gantry 313 or the ring 312 in the line segment L13. Specifically, when at least one of the rotational speeds of the gantry 313 and the ring 312 contained in the therapy plan is greater than the limit values, the control unit 240 reduces the rotational speed to a value less than the rotational speed in the therapy plan. At this time, the control unit 240 reduces the rotational speeds of the gantry 313 and the ring 312 while maintaining the ratio between the rotational speeds of the gantry 313 and the ring 312 which are indicated in the therapy plan.

The embodiment is not limited to a case in which the speed limitation map stored in the speed limitation map storage unit 232 illustrates only the existence and non-existence of a limitation to the rotational speeds. For example, the speed limitation map storage unit 232 may store a speed limitation map in which the rotational speed of the gantry 313 or the ring 312 is limited in three stages such as no speed limit, a high speed limit, and a low speed limit.

Alternatively, the speed limitation map storage unit 232 may store a speed limitation map illustrating a limit value for the rotational speed of the gantry 313, and a limit value for the rotational speed of the ring 312 for each rotational angle of the gantry 313 and each rotational angle of the ring 312.

The speed limitation map storage unit 232 is capable of storing various forms of speed limitation maps. For example, the speed limitation map storage unit 232 may store a speed limitation map in the form of a table illustrating the existence and non-existence of a limitation to the rotational speeds, or limit values for each rotational angle of the ring 312 and each rotational angle of the gantry 313.

Alternatively, the speed limitation map storage unit 232 may store a function having the rotational angles of the ring 312 and the gantry 313 as parameters, the output of which is the existence and non-existence of a limitation to the rotational speeds, or limit values.

Figure 4:
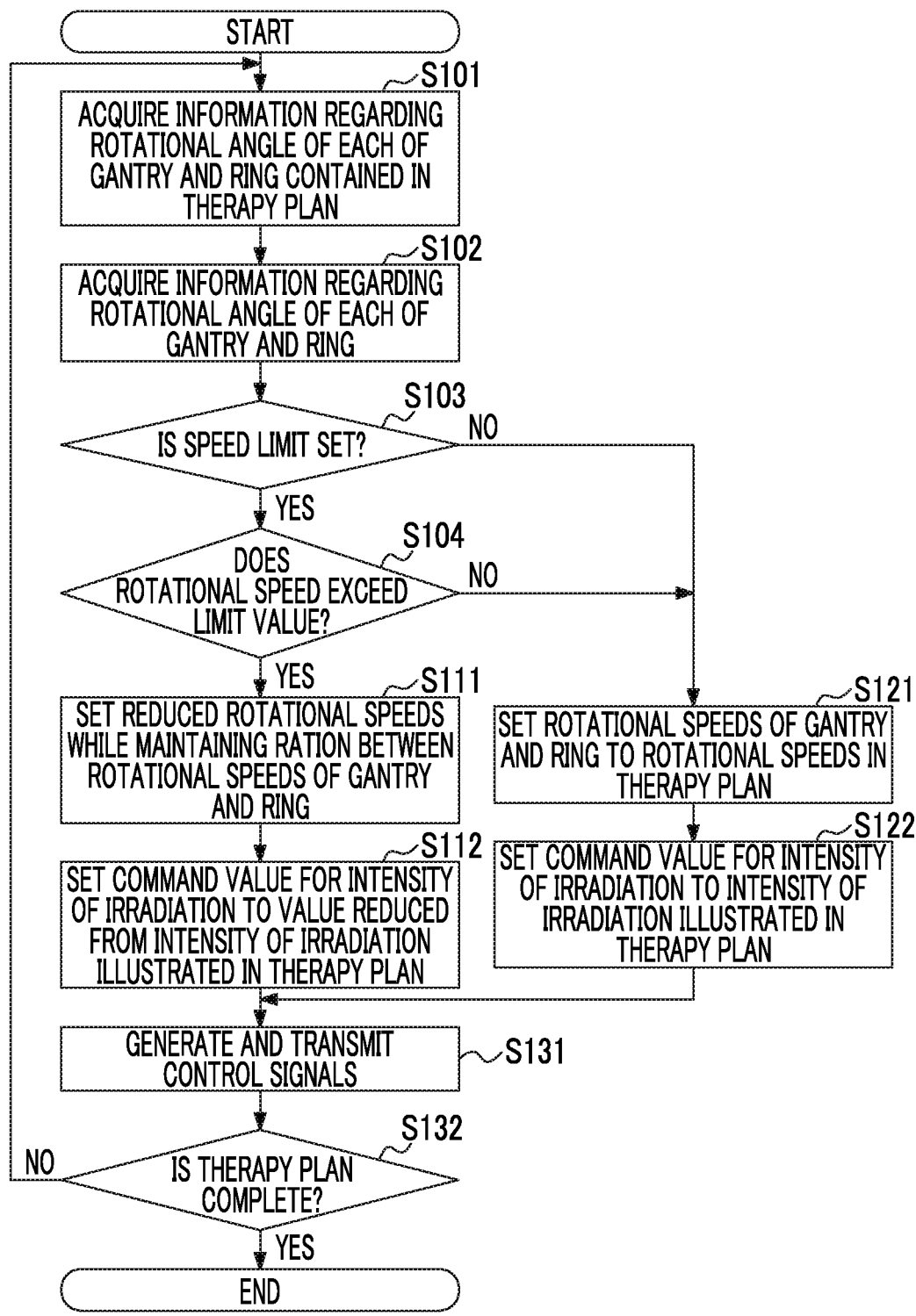
FIG. 4 is a flowchart illustrating an example of the sequence of a process by which a control unit 240 generates and transmits control signals to a radiation therapy device 30 in the embodiment.

Hereinafter, the operation of the device 20 for controlling a radiation therapy device will be described with reference to FIG. 4. FIG. 4 is a flowchart illustrating an example of the sequence of a process by which the control unit 240 generates controls signals to control the radiation therapy device 30. When the communication unit 290 receives the therapy plan from the therapy planning device 10, and the operation input unit 220 receives an operator's operation giving an instruction for the start of irradiation, the device 20 for controlling a radiation therapy device performs the process illustrated in FIG. 4.

In the process illustrated in FIG. 4, first, the control unit 240 acquires information regarding the rotational speed of each of the gantry 313 and the ring 312 contained in the therapy plan by reading a therapy plan stored in the therapy plan storage unit 231 (step S101).

Subsequently, the control unit 240 acquires information regarding the rotational angle of each of the gantry 313 and the ring 312 (step S102). For example, the control unit 240 acquires the information regarding the rotational angle of each of the gantry 313 and the ring 312 received by the communication unit 290 from the radiation therapy device 30.

The control unit 240 determines whether a limitation to the rotational speed is set for the rotational angle of each of the gantry 313 and the ring 312 in the speed limitation map stored in the speed limitation map storage unit 232 (step S103).

When the control unit 240 determines that a limitation to the rotational speeds is set (step S103: YES), the control unit 240 determines whether at least one of the rotational speeds of the gantry 313 and the ring 312 contained in the therapy plan exceeds the limit value (step S104).

Specifically, the control unit 240 compares the rotational speed of the gantry 313 in the therapy plan with the limit value which is set in advance for the rotational speed of the gantry 313.

In addition, the control unit 240 compares the rotational speed of the ring 312 in the therapy plan with the limit value which is set in advance for the rotational speed of the ring 312. The control unit 240 determines whether at least one of the rotational speeds of the gantry 313 and the ring 312 exceeds the limit value.

When the control unit 240 determines that at least one of the rotational speeds of the gantry 313 and the ring 312 exceeds the limit value (step S104: YES), the control unit 240 sets the rotational speeds of the gantry 313 and the ring 312 to be equal to or less than the limit values (step S111). At this time, the control unit 240 sets the rotational speeds of the gantry 313 and the ring 312 while maintaining the ratio between the rotational speeds contained in the therapy plan.

The control unit 240 sets a command value for the intensity of irradiation to a value which is reduced from the intensity of irradiation indicated in the therapy plan (step S112). When the rotational speeds of the gantry 313 and the ring 312 are reduced, an amount of time of therapeutic irradiation is lengthened so as to obtain an irradiation dose predetermined in the therapy plan. The control unit 240 adjusts the intensity of irradiation by controlling the opening of the multileaf collimator 332.

The control unit 240 generates control signals to control the radiation therapy device 30 based on the rotational speed of the gantry 313 or the ring 312 or the intensity of irradiation which is set, and transmits the control signals to the radiation therapy device 30 via the communication unit 290 (step S131).

Subsequently, the control unit 240 determines whether the execution of the therapy plan stored in the therapy plan storage unit 231 is complete (step S132). When it is determined that the execution of the therapy plan is not complete (step S132: NO), the process returns to step S101. In contrast, when it is determined that the execution of the therapy plan is complete (step S132: YES), the process in FIG. 4 ends.

In contrast, when, in step S103, the control unit 240 determines that no limitation to the rotational speeds is set (step S103: NO), the control unit 240 sets the rotational speeds of the gantry 313 and the ring 312 to the rotational speeds indicated in the therapy plan (step S121).

In addition, the control unit 240 sets a command value for the intensity of irradiation to the intensity of irradiation indicated in the therapy plan (step S122).

Thereafter, the process proceeds to step S131.

In contrast, when, in step S104, it is determined that neither the rotational speed of the gantry 313 nor the rotational speed of the ring 312 exceeds the limit value (step S104: NO), the process proceeds to step S121.

Also when the operation input unit 220 receives an operator's operation giving an instruction for the start of operation of the radiation therapy device 30 prior to the start of irradiation so as to confirm the path of the irradiation device 331, the control unit 240 controls the radiation therapy device 30 such that the gantry 313 and the ring 312 are operated. At this time, the control unit 240 generates control signals by which the gantry 313 and the ring 312 are instructed to rotate at the same rotational speeds in the process illustrated in FIG. 4, but the irradiation device 331 is instructed not to perform irradiation.

As described above, while maintaining the ratio between the rotational speeds of the gantry 313 and the ring 312 which are contained in the therapy plan, the control unit 240 sets a limitation to the rotational speeds of the gantry 313 and the ring 312 based on the rotational angles of the gantry 313 and the ring 312.

Accordingly, in a situation where caution is required to prevent contact between the irradiation device 331 and the couch 381, the control unit 240 is capable of moving the irradiation device 331 at a low speed while maintaining the movement path of the irradiation device 331 contained in the therapy plan. Since the irradiation device 331 moves at a low speed, when the irradiation device 331 is about to come into contact with the couch 381 or the like, the operator can prevent the occurrence of contact beforehand by stopping the radiation therapy device 30. Even if the irradiation device 331 comes into contact with the couch 381 or the like, it is anticipated that a loss such as damage to the irradiation device 331 or the couch 381 will not occur.

The speed limitation map storage unit 232 stores the speed limitation map illustrating the relationship between the rotational angles of the gantry 313 and the ring 312 and a limitation to the rotational speeds of the gantry 313 and the ring 312. The control unit 240 sets a limitation to the rotational speeds of the gantry 313 and the ring 312 based on the speed limitation map.

Accordingly, the control unit 240 is capable of understanding the necessity of limiting the rotational speed of the gantry 313 or the ring 312 by performing a simple step of reading information regarding a limitation to the rotational speeds corresponding to the rotational angles of the gantry 313 and the ring 312 from the speed limitation map.

The operation input unit 220 may receive an operation input giving an instruction for the movement speed of the irradiation device 331. In this case, while maintaining the ratio between the rotational speeds of the gantry 313 and the ring 312 contained in the therapy plan, the control unit 240 sets a limitation to the rotational speeds of the gantry 313 and the ring 312 based on the operation input and the rotational angles of the gantry 313 and the ring 312.

For example, when the operation input unit 220 includes a lever configured to receive an operation input regarding the movement speed of the irradiation device 331, the radiation therapy system 1 inputs the movement speed of the irradiation device 331 according to the inclination of the lever. The device 20 for controlling a radiation therapy device calculates the rotational speeds of the gantry 313 and the ring 312 according to the movement speed of the irradiation device 331 set by an operator's operation while maintaining the ratio between the rotational speeds of the gantry 313 and the ring 312 contained in the therapy plan.

The device 20 for controlling a radiation therapy device compares the calculated rotational speeds of the gantry 313 and the ring 312 with the limit values for the rotational speeds of the gantry 313 and the ring 312 contained in the speed limitation map, and controls the rotation of the gantry 313 and the ring 312 similarly to the process described with reference to FIG. 4.

Accordingly, an operator can confirm the movement path of the irradiation device 331 at a desired speed by performing a simple operation of controlling the inclination of the lever.

Even if the operator operates the irradiation device 331 at a relatively high speed, in a situation where caution is required to prevent contact between the irradiation device 331 and the couch 381, the control unit 240 reduces the movement speed of the irradiation device 331 while maintaining the ratio between the rotational speeds of the gantry 313 and the ring 312. Since the irradiation device 331 moves at a low speed, when the irradiation device 331 is about to come into contact with the couch 381 or the like, the operator can prevent the occurrence of contact beforehand by stopping the radiation therapy device 30. Even if the irradiation device 331 comes into contact with the couch 381 or the like, it is anticipated that a loss such as damage to the irradiation device 331 or the couch 381 will not occur.

The control unit 240 may move the irradiation device 331 reversely (that is, may rotate the gantry 313 or the ring 312 in a reverse direction) according to an operator's operation.

A program for realizing the entirety or a portion of the functions of the control unit 240 may be recorded on a computer readable recording medium, and a computer system may perform the process of each unit by reading and executing the program recorded on the recording medium. The "computer system" referred to here includes an OS or hardware such as peripheral equipment.

When the "computer system" uses the WWW system, the "computer system" also includes an environment under which a homepage is provided (environment under which a homepage is displayed).

The "computer readable recording medium" refers to portable media such as a flexible disk, a magneto-optical disk, a ROM, and a CD-ROM, and a storage device such as a hard disk built into the computer system. In addition, the "computer readable recording medium" also includes a communication line to dynamically hold the program for a short period of time when a program is transmitted via a network (for example, the Internet) or a communication channel (for example, a telephone channel), and a volatile memory in a server or a computer system (client) to hold the program for a predetermined amount of time. The program may realize a portion of the aforementioned functions, or may be able to realize the aforementioned functions in conjunction with a program stored in the computer system in advance.

The embodiment of the present invention has been described with reference to the drawings; however, the specific configuration is not limited to that in the embodiment, and design changes or the like can be made insofar as the design changes do not depart from the purport of the invention.

INDUSTRIAL APPLICABILITY

The present invention relates to a device for controlling a radiation therapy device which includes a gantry by which an irradiation device is supported in such a way as to be able to rotate around a first axial line, and a ring by which the gantry is supported in such a way as to be able to rotate around a second axial line intersecting with the first axial line, the device including: a movement path information storage unit configured to store information regarding a movement path set for the irradiation device; and a control unit configured to set a limitation to the rotational speeds of the gantry and the ring while maintaining the ratio between the rotational speed of the gantry and the ring, which is indicated by the information regarding the movement path, based on the rotational angles of the gantry and the ring.

According to the device for controlling a radiation therapy device, it is possible to more easily secure a path on which the radiation therapy device is capable of actually moving.

REFERENCE SIGNS LIST

1: RADIATION THERAPY SYSTEM
10: THERAPY PLANNING DEVICE
20: DEVICE FOR CONTROLLING RADIATION THERAPY DEVICE
210: DISPLAY UNIT
220: OPERATION INPUT UNIT
230: STORAGE UNIT
231: THERAPY PLAN STORAGE UNIT
232: SPEED LIMITATION MAP STORAGE UNIT
240: CONTROL UNIT
290: COMMUNICATION UNIT
30: RADIATION THERAPY DEVICE
312: RING
313: GANTRY
331: IRRADIATION DEVICE
390: COMMUNICATION UNIT
90: COMMUNICATION CHANNEL

The invention claimed is:

1. A device for controlling a radiation therapy device, the radiation therapy device including both a gantry by which an irradiation device is supported to be able to rotate around a first axial line, and a ring by which the gantry is supported in such a way as to be able to rotate around a second axial line intersecting with the first axial line, the device comprising:
a movement path information storage unit configured to store information regarding a movement path set for the irradiation device; and
a control unit configured to set a limitation to rotational speeds of the gantry and the ring while maintaining a ratio between rotational speeds of the gantry and the ring, which is indicated by the information regarding the movement path, based on rotational angles of the gantry and the ring.

2. The device for controlling a radiation therapy device according to claim 1, further comprising:
a speed limitation map storage unit configured to store a speed limitation map illustrating a relationship between the rotational angles of the gantry and the ring and a limitation to the rotational speeds of the gantry and the ring,
wherein the control unit sets a limitation to the rotational speeds of the gantry and the ring based on the speed limitation map.

3. The device for controlling a radiation therapy device according to claim 1, further comprising:
an operation input unit configured to receive an operation input giving an instruction for a movement speed of the irradiation device,
wherein the control unit sets a limitation to the rotational speeds of the gantry and the ring while maintaining the ratio between the rotational speeds of the gantry and the ring, which is indicated by the information regarding the movement path, based on the operation input and the rotational angles of the gantry and the ring.

4. A radiation therapy system comprising:
a gantry by which an irradiation device is supported to be able to rotate around a first axial line;
a ring by which the gantry is supported to be able to rotate around a second axial line intersecting with the first axial line;
a movement path information storage unit configured to store information regarding a movement path set for the irradiation device; and
a control unit configured to set a limitation to rotational speeds of the gantry and the ring while maintaining a ratio between a rotational speed of the gantry and the ring, which is indicated by the information regarding the movement path, based on rotational angles of the gantry and the ring.

5. A method for controlling a radiation therapy device via a device which includes a movement path information storage unit storing information regarding a movement path set for an irradiation device, the radiation therapy device including both a gantry by which the irradiation device is supported to be able to rotate around a first axial line, and a ring by which the gantry is supported to be able to rotate around a second axial line intersecting with the first axial line, the method comprising:

a control operation of setting a limitation to rotational speeds of the gantry and the ring while maintaining a ratio between the rotational speeds of the gantry and the ring, which is indicated by the information regarding the movement path, based on the rotational speeds of the gantry and the ring.

6. A non-transitory, computer-readable medium embodying a program causing a computer of a device to control a radiation therapy device, the radiation therapy device including both a gantry by which an irradiation device is supported to be able to rotate around a first axial line, and a ring by which the gantry is supported to be able to rotate around a second axial line intersecting with the first axial line, the device including a movement path information storage unit configured to store information regarding a movement path set for the irradiation device, the program causing the device to execute:

a control step of operation of setting a limitation to rotational speeds of the gantry and the ring while maintaining a ratio between the rotational speeds of the gantry and the ring, which is indicated by the information regarding the movement path, based on rotational angles of the gantry and the ring.

* * * * *